United States Patent [19]

Mia

[11] Patent Number: 5,036,047
[45] Date of Patent: Jul. 30, 1991

[54] METHOD AND COMPOSITION FOR PREVENTING CONCEPTION

[75] Inventor: Abdus S. Mia, Terre Haute, Ind.

[73] Assignee: Pitman-Moore, Inc., Lake Forest, Ill.

[21] Appl. No.: 250,557

[22] Filed: Sep. 29, 1988

[51] Int. Cl.⁵ ............................................. A61K 37/38
[52] U.S. Cl. ......................................... 514/15; 514/2; 514/800; 424/88; 530/807
[58] Field of Search ............... 514/2, 15, 800; 424/88; 530/313, 228, 807

[56] References Cited

U.S. PATENT DOCUMENTS

| | | | |
|---|---|---|---|
| 4,419,347 | 12/1983 | Nester et al. | 514/800 |
| 4,608,251 | 8/1986 | Mia | 514/19 |

OTHER PUBLICATIONS

PCT Int. App., 40 pp., Rigby et al., (1988), CA110(25) 226144.
Brit. UK. Pat. App. 8 pp., Morrison et al., CA110(25) 226143a, 1988.
PCT Int. Appl., 43 pp., Tilbrook, CA109(25) 223417m, (1988).
PCT Int. Appl., 19 pp., Brandon, CA110(17) 148783t, 1988.
Thau, Rosemarie B., Luteinizing Hormone-Releasing Hormone (LHRH) and Its Analogs for Contraception in Women: A Review, Contraception, vol. 29, No. 2, pp. 143-162 (1984).

*Primary Examiner*—John Doll
*Assistant Examiner*—T. D. Wessendorf
*Attorney, Agent, or Firm*—Wendell R. Guffey; Thomas L. Farquer

[57] ABSTRACT

A method for preventing conception in mammals which includes administering to the mammals a composition containing (1) free LHRH or its analog and (2) an immunogenic conjugate between LHRH or its analog and a carrier protein. Free LHRH or its analog acts to prevent conception in the mammal during the period from administration to about 6 weeks; the immunogenic conjugate acts to prevent conception during the period from about 6 weeks after administration until the LHRH antibodies formed in response to the conjugate are metabolized, generally about 0.5-2 years.

18 Claims, No Drawings

METHOD AND COMPOSITION FOR PREVENTING CONCEPTION

This invention relates generally to methods and compositions for preventing conception and particularly to a method and composition for using Luteinizing Hormone Releasing Hormone (LHRH) and its analogs to prevent conception in mammals.

BACKGROUND OF THE INVENTION

Luteinizing Hormone Releasing Hormone (LHRH) is secreted by the hypothalamus and carried to the pituitary gland where it stimulates secretion of follicle stimulating hormone and luteinizing hormone which, in turn, stimulate ovarian follicle development, the conversion of ovarian follicle to corpus luteum, tubule development in the testicles, and production of progesterone and testosterone. Thus, release of LHRH from the hypothalamus causes ovulation and the formation of corpus luteum in females and causes spermatogenesis in males.

LHRH is a decapeptide having the following structure: pGlu-His-Trp-Ser-Tyr-Gly-Leu-Arg-Pro-Gly-NH$_2$, wherein, according to convention, the amino group of each amino acid appears to the left and the carboxyl to the right with the hydroxyl of the carboxyl of the terminal Gly being replaced by an NH$_2$ group. The conventional abbreviations for the amino acids are: Glu (glutamic acid), pGlu (pyroglutamic acid), His (histidine), Trp (tryptophan), Ser (serine), Tyr (tyrosine), Gly (glycine), Leu (leucine), Arg (arginine), Pro (proline), Lys (lysine) and Cys (cysteine). Except for glycine which has no optical center, all amino acids are of the L-configuration unless otherwise indicated. LHRH may be produced as described in U.S. Pat. Nos. 4,159,980 and 4,213,895.

U.S. Pat. Nos. 3,880,825; 3,941,763; 4,034,082; 4,072,668; 4,075,192; 4,143,133; 4,143,136; 4,211,769; 4,234,571; and 4,263,282 disclose analogs of LHRH which act as agonists or antagonists of LHRH. U.S. Pat. No. 4,010,261 discloses administering LHRH analogs to an animal in amounts such as 2-200 micrograms per kilogram of body weight to effect the reproductive cycle.

LHRH and its several analogs have been studied as potential agents for fertility control. Free LHRH or its agonists, when administered frequently and in comparatively high doses, exhibit antifertility effect. (Contraception, 24:647-655 (1981) and Fertility Sterility, 38:190-193 (1982). Also, repeated administration of potent antagonist may be used for antifertility effect. LHRH and its agonists work by pituitary desensitization, whereas the antagonists act by competitive inhibition. Antifertility and other antigonadotropic effects of high doses of LHRH and its agonists or the antagonist analogs are immediate but of short duration, requiring frequent administration. Thus they are not of practical use for veterinary or wildlife use as such. In addition, in some cases, large amounts of the analogs may cause unwanted and adverse side effects.

LHRH or its appropriate analogs conjugated to carrier proteins can also be administered to an animal as an antigen to induce the formation of host antibodies to LHRH; the antibodies will subsequently act against the body's own LHRH. Thus, a long term antigonadic effect is established. Using LHRH or various LHRH analogs as antigens is described in the literature: Arimura et al., *Endocrinology*, 93:1092-1103(1973); Fraser et al., *Journal of Endocrinoloqy*, 63:399-406 (1974); Jeffcoate et al., *Immunochemistry*, Vol. 11, p. 75-77 (1974); Clarke et al., *Journal of Endocrinology*, 78:39-47 (1978); Johnson et al., *Animal Science*, 66:719-726 (1988); Falvo et al., *Animal Science*, 63:986-994 (1986); Pique et al., *Immunochemistry*, Vol. 15, p. 55-60 (1978); Stevens et al., *American Journal of Reproductive Immunology*, 1:307-314 (1981); and in U.S. Pat. No. 3,963,691. U.S. Pat. No. 4,608,251 discloses LHRH analogs useful for stimulating anti-LHRH antibodies and the vaccines using such analogs.

LHRH or its analogs are usually administered via a vaccine after conjugation to immunogenic carriers to a mammal to stimulate the immune system to produce anti-LHRH antibodies which react with LHRH to effectively reduce its concentration in the body. The effects caused by the presence of LHRH are thus reduced or eliminated, including ovulation and formation of corpus luteum in females and spermatogenesis in males. The anti-LHRH antibodies induced by LHRH or its analogs thus effectively prevent conception by reducing the amount of LHRH in the body.

This technique is, however, not totally effective in preventing conception for an initial period of variable length following injection. The production of antibodies in sufficient amounts to reduce the LHRH concentration to a level that can prevent conception generally takes about 4-6 weeks or more. During that lag period, unwanted conception may occur. A method is, therefore, needed which can prevent conception during the lag period as well as prevent conception during metabolic life of the induced antibodies. Such a method is needed to prevent conception in cases of unwanted pregnancies, particularly for domestic/stray pets and wild animals.

At present there are 43 million dogs and 31 million cats in the United States and their numbers increase daily. Stray dogs and cats along with wild animals such as skunks and raccoons are known to be major sources of rabies transmission to domestic animals and humans. Surgical removal of reproductive organs, e.g., spaying and castration, is presently a commonly used method for preventing reproduction in such animals. However, surgery is relatively costly, time consuming and impractical when used with wild or stray animals. Prevention of the explosive population increase of wild animals, including deer and horses in park and forest preserves, requires a practical and acceptable method of birth control for wild and free ranging animals.

SUMMARY OF THE INVENTION

It is, therefore, an object of the present invention to provide a method for preventing conception in mammals.

It is another object of the present invention to provide a composition for preventing conception in mammals.

It is another object of the present invention to provide a kit useful for preventing conception in mammals.

It is another object of the present invention to provide a method for preventing conception in mammals soon after administration of the composition.

It is another object of the present invention to provide a method for preventing conception in mammals for extended periods.

It is another object of the present invention to provide a method for preventing conception in mammals which is reversible.

It is another object of the present invention to provide a method for preventing conception in mammals during the lag period characteristic of prior art vaccine methods.

These and other objects are achieved by administering to mammals a composition comprising (1) free LHRH or an analog thereof and (2) an immunogenic conjugate between a protein and LHRH or an analog thereof.

In the preferred embodiment, free LHRH or its analog and the immunogenic conjugate are administered in a "vaccine" as disclosed in U.S. Pat. No. 4,608,251. The "vaccine" is formulated as disclosed in the referenced patent except that LHRH or its analog is incorporated into the vaccine formulation in amounts sufficient to prevent conception during the "lag" period between administration of the "vaccine" and the time at which the anti-LHRH antibody titer produced in response to the conjugate is sufficient to prevent conception. Typically, the "vaccine" (injectable formulation) of free LHRH or its analog and the conjugate contains free LHRH or its analog in amounts sufficient to supply a dosage of from about 0.1-2 milligrams per kilogram of body weight (mg/kg) free LHRH or its analog and a dosage of from about 0.01-2 mg/kg of the conjugate.

Free LHRH or its analog acts to prevent conception in the mammal during the period from administration to about 6 weeks; the immunogenic conjugate acts to prevent conception during the period from about 6 weeks after administration until the LHRH antibodies formed in response to the conjugate are metabolized, generally about 0.5-2 years. The water in oil emulsion disclosed in U.S. Pat. No. 4,608,251 acts as an adjuvant for the vaccine and as a slow release vehicle for the free LHRH or its analog.

Most preferably, a composition comprising (1) free LHRH or an analog thereof and (2) an immunogenic conjugate between a protein and a nonapeptide of the formula:

Lys-Trp-Ser-Tyr-Gly-Leu-Arg-Pro-Gly-NH$_2$ or decapeptide of the formula:

Cys-Lys-Trp-Ser-Try-Gly-Leu-Arg-Pro-Gly-NH$_2$ or mixtures thereof is administered to mammals to prevent conception over the period from initial injection to about 2-3 years.

Other objects, advantages, and novel features of the present invention will become apparent from the following detailed description of the invention.

DETAILED DESCRIPTION OF THE INVENTION

The term "free LHRH or its analog" as used herein includes all peptides having LHRH bioactivity including natural, synthetic, recombinant, and mutein peptides having deleted, elongated, replaced, or otherwise altered amino acid sequences and other compounds which function as LHRH analogs.

The term "LHRH or its analog" as used herein includes all peptides having LHRH immunogenicity including natural, synthetic, recombinant, and mutein peptides having deleted, elongated, replaced, or otherwise altered amino acid sequences.

According to the present invention, a method for preventing conception in mammals comprises administering to the mammals a composition comprising (1) free LHRH or its analog and (2) an immunogenic conjugate between a protein and LHRH or its analog.

The conjugate acts as an immunogen for LHRH which induces the mammalian immune system to produce antibodies which react with LHRH; immunization against LHRH produces antibodies which react with LHRH to lower the male and female endogenous LHRH concentration and prevent conception. Free LHRH or its agonist analogs, when administered in relatively large dosages, act as antifertility agents by desensitizing the pituitary to the normal effects of LHRH. LHRH antagonists act as antifertility agents by competing with LHRH for its receptors thus lowering the effective LHRH concentration.

Free LHRH or its analog acts to prevent conception in the mammal during the period from administration to about 6 weeks; the conjugate acts to prevent conception during the period from about 6 weeks after administration until the LHRH antibodies formed in response to the conjugate are metabolized, generally about 0.5-2 years. Thus, the combination of free LHRH or its analog and the immunogenic conjugate of LHRH or its analog can prevent conception from the time of administration; conception does not occur during the lag period between administration and the formation of sufficient anti-LHRH antibodies to prevent conception.

Free LHRH or its analogs can be obtained from any suitable source, all well known in the art. For example, U.S. Pat. Nos. 4,159,980 and 4,213,895, incorporated herein by reference, disclose methods for preparing LHRH or its analogs. Other methods for producing, isolating, and purifying native and synthetic LHRH or its analogs are well known in the art.

The immunogenic conjugate comprising the protein and LHRH or its analog is obtained using the method disclosed in U.S. Pat. No. 4,608,251, incorporated herein by reference. Other methods for producing hapten-carrier conjugates from peptides such as LHRH are well known to the art.

Although the dosages of free LHRH or its analog and the conjugate vary according to the age, size, and character of the particular mammal and the compound administered, free LHRH or its analog is typically administered to the mammal in dosages of from about 0.1-2 milligrams per kilogram of body weight (mg/kg), preferably from about 0.2-1 mg/kg, and the conjugate is typically administered to the mammal in dosages of from about 0.01-2 mg/kg, preferably from about 0.2-1 mg/kg. The compounds can be administered in a single dosage or, more preferably, administered in two dosages at 6-8 week intervals.

Free LHRH or its analog and the immunogenic conjugate according to the present invention can be administered to the mammal in any acceptable manner including by injection, using an implant, and the like. Injections and implants are preferred because they permit precise control of the timing and dosage levels used for administration. LHRH or its analog and the conjugate according to the present invention are preferably administered parenterally. As used herein parenteral administration means by intravenous, intramuscular, or intraperitoneal injection, or by subcutaneous implant.

Free LHRH or its analog and the immunogenic conjugate are preferably administered to the mammal by (1) administering free LHRH or its analog and conjugate in a "vaccine" as described in U.S. Pat. No. 4,608,251, (2) administering the conjugate in a "vaccine" as described in U.S. Pat. No. 4,608,251 and administering the free LHRH or its analog in a separate injectable formulation or implant as described below, or (3) by formulating the free LHRH or its analog and conjugate into a single injectable formulation as described below.

Most preferably, free LHRH or its analog is simply incorporated into the "vaccine" disclosed in U.S. Pat. No. 4,608,251 in amounts sufficient to prevent conception during the "lag" period between administration of the "vaccine" and the time at which the anti-LHRH antibody titer is sufficient to prevent conception. This generally involves incorporating free LHRH or its analog and conjugate into a water-in-oil (w/o) emulsion containing about 0.5–200 mg free LHRH or its analog and about 0.05–200 mg of the conjugate, depending on the mammal's body weight. Both the free LHRH or its analog and the conjugate are contained in microscopic water droplets surrounded by the continuous oil phase. The w/o emulsion thus serves as an adjuvant for the conjugate and as a controlled release carrier which releases free LHRH or its analog slowly into the body after administration.

When administered by injection, free LHRH or its analog and/or the immunogenic conjugate can be administered to the mammal in a injectable formulation containing any biocompatible and free LHRH or its analog and conjugate compatible carrier such as various vehicles, adjuvants, additives, and diluents.

Aqueous vehicles such as water having no nonvolatile pyrogens, sterile water, and bacteriostatic water are also suitable to form injectable solutions. In addition to these forms of water, several other aqueous vehicles can be used. These include isotonic injection compositions that can be sterilized such as sodium chloride, Ringer's, dextrose, dextrose and sodium chloride, and lactated Ringer's.

Nonaqueous vehicles such as cottonseed oil, sesame oil, or peanut oil and esters such as isopropyl myristate may also be used as solvent systems for the compositions.

Additionally, various additives which enhance the stability, sterility, and isotonicity of the composition including antimicrobial preservatives, antioxidants, chelating agents, and buffers can be added. Any vehicle, diluent, or additive used would, however, have to be biocompatible and compatible with free LHRH or its analog and the immunogenic conjugate according to the present invention.

Free LHRH or its analog according to the present invention can be administered to the mammal in the form of a slow-release subcutaneous implant which is inserted beneath the skin of the mammal. The implant can take the form of a pellet which slowly dissolves after being implanted in the mammal or a biocompatible and mammal compatible delivery module well known to those skilled in the art. Such well known dosage forms are designed such that the active ingredients are slowly released over a period of several days to several weeks, preferably a larger amount of free LHRH or its analog is released initially and the amount decreases with time. The implant is designed to deliver from about 0.002–0.04 mg/kg/day initially, preferably from about 0.005–0.02 mg/kg/day. The implant should be inserted into the mammal about the same time as the vaccine according to U.S. Pat. No. 4,608,251 is administered.

Although not required, the formulations of the present invention can be administered two or more times during the initial 4–6 week period. Preferably, the formulations are administered twice at a 3 to 6 week interval to insure that the free LHRH or its analog is present in the body in sufficient concentration to prevent conception and to insure that there is sufficient conjugate to initiate a strong immune response. According to the method in U.S. Pat. No. 4,608,251, an annual booster vaccine containing the same dose of conjugate is recommended for a continued effect.

In a preferred embodiment, a composition comprising (1) free LHRH or an analog thereof and (2) an immunogenic conjugate between a protein and a nonapeptide of the formula:

Lys-Trp-Ser-Tyr-Gly-Leu-Arg-Pro-Gly-NH$_2$ or decapeptide of the formula:

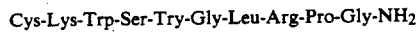
Cys-Lys-Trp-Ser-Try-Gly-Leu-Arg-Pro-Gly-NH$_2$ or mixtures thereof is administered to mammals in a "vaccine" as disclosed in U.S. Pat. No. 4,608,251 to prevent conception over the period from initial injection to about 2–3 years. The "vaccine" is formulated as disclosed in the patent except that free LHRH or its analog is incorporated into the vaccine formulation in amounts sufficient to prevent conception during the "lag" period between administration of the "vaccine" and the time at which the anti-LHRH antibody titer is sufficient to prevent conception; typically, from about 0.1–2 mg/kg LHRH or its analog and from about 0.01–2 mg/kg of the conjugate.

Since free LHRH or its analog and the immunogenic conjugate can be administered separately, the present invention also contemplates an article of manufacture in the form of a kit comprising in separate containers in a single package (1) free LHRH or its analog and (2) an immunogenic conjugate between a protein and LHRH or its analog. The kit should contain free LHRH or its analog in amounts sufficient to supply from about 0.1–2 mg/kg/day free LHRH and the conjugate in amounts sufficient to supply from about 0.1–2 mg/kg/day conjugate when administered to said mammals.

Free LHRH or its analog and the immunogenic conjugate according to the present invention are used to prevent short term (0–6 weeks after administration) and long term (greater than 6 weeks after administration) conception in mammals, respectively.

The composition, kit and method herein are also defined to include various combinations and mixtures of free LHRH and/or its analogs in combination with various combinations and mixtures of immunogenic conjugates of LHRH and/or its analogs.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Eight groups of young adult female rats having 4 or 5 members per group were given intramuscular injections of 0.2 milliliters of preparations containing free LHRH, Lys-Trp-Ser-Tyr-Gly-Leu-Arg-Pro-Gly-NH$_2$ (LysLHRH), a LysLHRH-KLH conjugate, or combinations of these as shown in Table 1. Fertile male rats were put with the treated females within 24 to 48 hours after treatment and were observed for 105 days. Periodical blood samples were taken for antibody titers. At the end of trial, the female animals were sacrificed and their reproductive organs examined. The results are shown in Table 1.

Referring to Table 1, group 1 shows that LHRH prevents conception for a period of 6 weeks after administration, group 2 shows no efficacy to prevent pregnancy, group 3 shows that conception is prevented by the combination of LHRH and a LysLHRH-KLH (LysLHRH conjugated to Keyhole Limpet Hemocyanin) conjugate for the entire study period, group 4 shows that LysLHRH-KLH prevented pregnancy after the lag period during which all rats became pregnant, group 5 shows that slightly lower LHRH dosages can be effective for preventing conception (as compared to Group 3), groups 6 and 7 show that ½ dose and ¼ dose (as compared to Group 3) are effective for preventing conception, and group 8 is a control using a placebo. All rats were presumed fertile before treatment.

Although not wishing to be bound by theory, it appears that failure of free LysLHRH (group 2) to prevent pregnancy is due to its greatly reduced biological activity of LHRH due to the elimination of pyroglutamic acid and substitution of lysine for histadine, although it retained the immunological identity of LHRH. Pregnancy of all rats in group 4 during the initial six weeks followed by no pregnancy confirms the lack of biological activity of LysLHRH as observed in group 2 and the existence of a lag period of the conjugate.

LHRH in high dose prevented pregnancy by desensitization as observed by frequent injection or constant infusion. Use of water-in-oil (w/o) adjuvants allows slow continuous prolonged release of LHRH simulating frequent injection or constant infusion. The present invention prevents conception for extended periods following a single injection in which combined effects of frequent injection or infusion of LHRH on the active immunization against LHRH are obtained. Although only a combination of LHRH and LysLHRH-KLH conjugate in a water-in-oil emulsion has been used in this example, other combinations of appropriately potent LHRH analogs and their conjugates may likewise be used.

Approximately 4-6 weeks is regarded as the time required to develop anti-LHRH antibody titers sufficient to prevent conception after injection of LysLHRH-KLH conjugate in w/o adjuvant.

Obviously many modifications and variations of the present invention are possible in light of the above teachings. It is therefore to be understood that within the scope of the appended claims the invention may be practiced otherwise than as specifically described.

TABLE 1

| Group | Treatment with Dose all in w/o adjuvant | Number of Animals | Pregnancies Weeks 1-6 | Pregnancies Weeks 7-15 | Uterus Condition |
|---|---|---|---|---|---|
| 1 | LHRH 0.5 mg | 4 | 0/4 | 2/4 | normal-3 slight atrophy-1 |
| 2 | LysLHRH 0.5 mg | 4 | 4/4 | 4/4 | normal-4/4 |
| 3 | LHRH 0.25 mg + LysLHRH-KLH 0.25 mg | 4 | 0/4 | 0/4 | atrophy-4/4 |
| 4 | LysLHRH 0.25 mg + LysLHRH-KLH 0.25 mg | 4 | 4/4 | 0/4 | atrophy-4/4 |
| 5 | LHRH 0.20 mg + LysLHRH-KLH 0.1 mg | 5 | 0/5 | 0/5 | atrophy-5/5 |
| 6 | LHRH 0.1 mg + LysLHRH-KLH 0.1 mg | 5 | 0/5 | 0/5 | atrophy-5/5 |
| 7 | LHRH 0.05 mg + LysLHRH-KLH 0.1 mg | 5 | 1/5 | 0/5 | atrophy-5/5 |
| 8 | KLH 0.25 mg | 5 | 5/5 | 5/5 | normal-5/5 |

What is claimed is:

1. A method for preventing conception in mammals, consisting essentially of:
    administering to said mammals a composition consisting essentially of (1) free LHRH which acts to prevent conception in the mammal during the period from administration to about 6 weeks and (2) an immunogenic conjugate between a protein and LHRH selected from the group consisting of a formula:

Lys-Trp-Ser-Tyr-Gly-Leu-Arg-Pro-Gly-NH$_2$ and

Cys-Lys-Trp-Ser-Tyr-Gly-Leu-Arg-Pro-Gly-NH$_2$ or mixtures thereof, which acts to prevent conception during the period from about 6 weeeks after administration until the LHRH antibodies formed in response to the conjugate are metabolized, about 0.5-2 years.

2. The method of claim 1 wherein said protein is Keyhole Limpet Hemocyanin.

3. The method of claim 1 wherein said free LHRH is administered in amounts of from about 0.1-2 mg/kg/day and said conjugate is administered in amounts of from about 0.1-2 mg/kg/day.

4. The method of claim 1 wherein said composition is administered parenterally.

5. The method of claim 4 wherein said composition is administered in an, injectable formulation, said injectable formulation consisting essentially of a biocompatible and composition compatible carrier and a conception preventing amount of said composition.

6. The method of claim 5 wherein said carrier is a water-in-oil emulsion.

7. The method of claim 1 wherein said free LHRH and said conjugate are administered separately.

8. The method of claim 7 wherein (1) said free LHRH is administered using an implant, said implant consisting essentially of a biocompatible and free LHRH compatible implant material and a conception preventing amount of said free LHRH and (2) said conjugate is administered using an injectable formulation, said injectable formulation consisting essentially of a biocompatible and conjugate compatible carrier and a conception preventing amount of said conjugate.

9. The method of claim 7 wherein (1) said free LHRH is administered using an injectable formulation, said injectable formulation consisting essentially of a biocompatible and free LHRH compatible carrier and a conception preventing amount of said free LHRH and (2) said conjugate is administered using an injectable formulation, said injectable formulation consisting essentially of a biocompatible and conjugate compatible carrier and a conception preventing amount of said conjugate.

10. A composition for preventing conception in mammals, consisting essentially of (1) free LHRH and (2) an immunogenic conjugate between a protein and LHRH selected from the group consisting of a formula:

Lys-Trp-Ser-Tyr-Gly-Leu-Arg-Pro-Gly-NH$_2$ and

Cys-Lys-Trp-Ser-Tyr-Gly-Leu-Arg-Pro-Gly-NH$_2$ or mixtures thereof.

11. The composition of claim 10 wherein said protein is Keyhole Limpet Hemocyanin.

12. The composition of claim 10 consisting essentially of said free LHRH in amounts sufficient to supply from about 0.1-2 mg/kg/day LHRH and said conjugate in amounts sufficient to supply from about 0.1-2 mg/kg/day conjugate when administered to said mammals.

13. The composition of claim 10 in the form of an injectable formulation, said injectable formulation consisting essentially of a biocompatible and composition compatible carrier and a conception preventing amount of said free LHRH and conjugate.

14. The composition of claim 13 in the form of a "vaccine" which consists essentially of said free LHRH and conjugate in a water-in-oil emulsion.

15. The composition of claim 10 wherein (1) said free LHRH is in the form of an implant, said implant consisting essentially of a biocompatible and free LHRH compatible implant material and a conception preventing amount of said free LHRH and (2) said conjugate is in the form of an injectable formulation, said injectable formulation comprising a biocompatible and composition compatible carrier and a conception preventing amount of said conjugate.

16. The composition of claim 10 wherein (1) said free LHRH is in the form of an injectable formulation, said injectable formulation consisting essentially of a biocompatible and free LHRH compatible carrier and a conception preventing amount of said free LHRH and (2) said conjugate is in the form of an injectable formulation, said injectable formulation consisting essentially of a biocompatible and conjugate compatible carrier and a conception preventing amount of said conjugate.

17. A kit consisting essentially of in separate containers in a single package (1) free LHRH selected from the group consisting of a formula:

Lys-Trp-Ser-Tyr-Gly-Leu-Arg-Pro-Gly-NH$_2$ and

Cys-Lys-Trp-Ser-Tyr-Gly-Leu-Arg-Pro-Gly-NH$_2$ or mixtures thereof and (2) an immunogenic conjugate between a protein and LHRH or its, analog.

18. The kit of claim 17 consisting essentially of said free LHRH in amounts sufficient to supply from about 0.1-2 mg/kg/day free LHRH and said conjugate in amounts sufficient to supply from about 0.1-2 mg/kg/day conjugate when administered to said mammals.

* * * * *